United States Statutory Invention Registration [19]

[11] Reg. Number: H726

Brown et al. [43] Published: Jan. 2, 1990

[54] 2,4-BIS-ARYLOXY-M-PHENYLENEDIAMINES AND THEIR USE AS COUPLERS IN OXIDATION DYE COMPOSITIONS

[75] Inventors: Keith C. Brown, New Canaan; James E. Kijek, Danbury, both of Conn.

[73] Assignee: Clairol Incorporated, New York, N.Y.

[21] Appl. No.: 1,721

[22] Filed: Jan. 9, 1987

[51] Int. Cl.[4] ..... C07C 93/14; C07C 149/42

[52] U.S. Cl. ..... 564/428; 564/430; 8/408; 8/411; 8/416

[58] Field of Search ..... 564/428, 430; 8/408, 8/411, 416

[56] References Cited

U.S. PATENT DOCUMENTS

| | | | |
|---|---|---|---|
| 3,133,086 | 5/1964 | Bossard et al. | 564/417 |
| 4,171,203 | 10/1979 | Rose et al. | 564/430 |
| 4,566,876 | 1/1986 | Brown et al. | 564/430 |

OTHER PUBLICATIONS

J. Chem. Soc. J. F. Corbett, (B), 1970, pp. 1418–1427.
J. Chem. Soc. J. F. Corbett, 1972, pp. 999–1005.
J. Soc. Cosmet. Chem., 24, (Feb. 2, 1973), pp. 103–134.
J. F. Corbett, "p-Benzoquinonediimine . . . " J. Soc. Cosmetic Chemists, 20, pp. 253–263 (1969).

*Primary Examiner*—John F. Terapane
*Assistant Examiner*—Richard Treavor

[57] ABSTRACT

Compounds of formula:

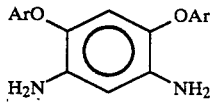

and oxidation hair dye compositions containing the same; also includes a process for dyeing hair with such compositions; Ar being an aryl radical.

15 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

2,4-BIS-ARYLOXY-M-PHENYLENEDIAMINES AND THEIR USE AS COUPLERS IN OXIDATION DYE COMPOSITIONS

This invention relates to certain novel oxidation dye couplers that are useful in oxidation dye systems. More particularly, it concerns dye couplers (also sometimes known as meta components) of the aforesaid type that are designed to be used in conjunction with the so called oxidation dye primary intermediates to dye a substrate as, for example, human hair. Although the dye couplers of the present invention have a variety of uses, for purposes of convenience they will be described with reference to their primary intended use, namely, in the dyeing of hair and especially dyeing hair on the human head.

Oxidation dye systems are widely used in dyeing hair, especially in dyeing hair on the human head. Such dye systems generally comprise one or more primary dye intermediates (also referred to as primary intermediates or para components) which are able to dye hair in the presence of an oxidizing agent. This process is often referred to as color development, the oxidizing agent being designated as the color developer.

However, because of the limitation in the range of colors that can be obtained with primary intermediates alone, the art has adopted the use of color couplers which have the capacity to modify the colors of the primary intermediates when applied to hair in the presence of an oxidizing agent. These couplers are characterized by the fact that when used by themselves they usually do not develop a color under oxidizing conditions. However, when employed in conjunction with a primary intermediate or a combination of primary intermediates they will modify the color that the primary intermediates would ordinarily develop on hair. These couplers are known to react chemically with the primary intermediate to develop dyes. In oxidation hair dye systems it is common to also have one or more couplers included in such systems. The couplers of the present invention may be used in oxidation dye systems of this character.

The present invention provides novel color couplers for oxidation dye systems, and particularly "red" couplers, that have a variety of advantages over the known prior art color couplers. For example, many of the meta-aminophenol derivatives when employed as color couplers in conjunction with primary intermediates form dyes for which the "color take" on hair is only weak. The evidence appears to indicate that this weakness in color uptake is due to the fact that the meta-aminophenolate anion is repelled by the hair at the pH at which the dyeing takes place. This apparently slows the rate of diffusion of the coupler into the hair. A number of the couplers of this invention avoid this problem and give strong dyeings to hair when used with primary intermediates in oxidation dye systems.

Also many of the couplers used in the prior art for producing red shades are themselves reactive towards hydrogen peroxide which results in a significant, non-color forming, loss of these couplers during the dyeing process. These reactions do not occur with the couplers of this invention and as a consequence stronger dyeings occur. Moreover, phenolic couplers (e.g. 1-naphthol) which are generally used to give violet-blue colors require high concentrations in use because they are reactive towards $H_2O_2$ and are destroyed during the dyeing process. By using the couplers of the present invention a significantly better utilization of the phenolic couplers is obtained. The phenolic moieties are present in bound or protected form in the couplers of this invention. They are therefore less subject to destructive reaction with $H_2O_2$. After diffusing into the hair the phenolic moieties are freed from the bound form and are available for reaction as phenolic couplers with the primary intermediates.

Another advantage of couplers embodied in the present invention is that some have been demonstrated to provide dyeings of significant shampoo fastness. Still a further advantage is the fact that the dyeings obtained with the couplers of this invention in oxidation dye systems are drabber colors which give a more natural appearance to the hair. The importance of this feature in the hair dye art is pointed out at page 253 in the book entitled "The Science of Hair Care" edited by Charles Zviak. As will be discussed in more detail below this is due to that fact that under certain conditions of concentration the couplers of the present invention provide two competing coupling reaction with the primary intermediates leading to the formation of a mixture of dyes. This mixture of dyes therefore gives the drabbing result since a combination of colors is produced.

The couplers of the present invention may be described by the formula:

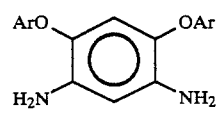

(I)

wherein the Ar's are the same or different aryl radicals. As used herein the term aryl is employed in its broad sense to include aromatic radicals that may be substituted or unsubstituted monocylic or polycylic radicals. Usually, however, the aryl radical Ar will be a substituted or unsubstituted monocylic or bicyclic aromatic radical having up to about 6 to 10 carbon atoms in the ring structure. The substituent groups, when present on the aromatic rings may also be varied. Thus, for example, they may be one or more alkyl groups (preferably lower alkyl groups containing 1 to 5 carbon atoms) alkoxy groups—OR, where R may be alkyl (preferably lower alkyl containing 1 to 5 carbon atoms) or a hydroxy alkyl (also preferably containing 1 to 5 carbon atoms, amino, halo, hydroxy etc. or mixtures thereof. By way of illustration of the aryl groups represented by Ar in formula (I) mention may be made of the following: phenyl, 1-naphthyl, 2-methylphenyl, 2,6-dimethylphenyl, 3-aminophenyl, 3-amino-6-methylphenyl, 3-hydroxyphenyl, 2-methyl-3-hydroxyphenyl, etc.

The oxidation dye couplers of the present invention may be prepared by a variety of synthetic routes. One synthetic route that has proven to be very satisfactory is accomplished in three stages. In the first a m-dihalobenzene (e.g. m-dichlorobenzene) is nitrated (for example) with a mixture of fuming $HNO_3$ and conc. $H_2SO_4$. This introduces two nitro groups into the benzene ring, each in a position which is para to a halogen atom on the ring to form a 2,4-dinitro-1,5 dihalobenzene.

The reaction product of the first stage e.g. 2,4-dinitro-1,5-dihalobenzene is used as a starting material for the second stage of the synthesis. This is reacted with an alkali metal phenolate which has the general formula ArOM wherein Ar is an aryl radical as described above and M is an akali metal, preferably sodium. In the preferred form of this invention the alkali metal phenolate is formed in situ in the reaction mixture by the reaction of an alkali metal hydroxide, e.g. NaOH, with a phenol of the formula ArOH where Ar is an aryl having the significance ascribed to it before. The reaction of stage two is generally carried out in a solvent. The reactants may be employed in the molar ratio of 1 mole of the 2,4-dinitro-1,5 dihalobenzene to about 2.0 moles to about 3.0 moles of the alkali metal phenolate with the preferred molar ratio being from about 1 mole of 2,4-dinitro-1,5-dihalobenzene to about 2.0 moles to about 2.1 moles of the alkali metal phenolate. The reaction will ordinarily be carried out at reflux conditions. In the second stage of the process a phenolate radical ArO— replaces each of the halogen atoms on the benzene radical of the 2,4,dinitro-1,5-dihalobenzene second stage starting material. The products of this reaction are 4,6-diaryloxy-1,3-dinitrobenzenes.

The starting material of the third stage of this process is the 4,6-diaryloxy-1,3-dinitrobenzene obtained from the second stage. This involves the catalytic reduction of each of the nitro groups in the starting material. In a preferred form of this invention this involves hydrogenating the starting material, usually in a solvent system, in the presence of a hydrogenating catalyst e.g. Pt/C.

The process described above can be summarized by the following equations:

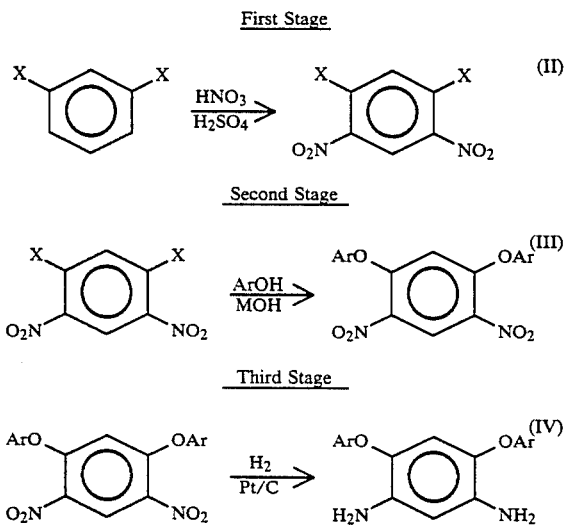

In these equations X is halogen, preferably Cl; Ar is aryl as defined above; and M is alkali metal, preferably Na.

As indicated above the oxidation dye couplers of this invention are useful in dyeing human hair, particularly on the head. In this case one or more of the present couplers will be incorporated in a dye concentrate which is intended to be mixed with, for example, aqueous hydrogen peroxide just before application to the hair. The quantity of the present dye coupler that may be contained in said dye concentrate may vary depending upon the quantity of primary oxidation dye intermediate or intermediates, the quantity (if any) of any other coupler or couplers that may be contained in the dye concentrate, as well as the desired results. However, generally the dye concentrate will contain from about 0.01% to about 10% by weight of the dye coupler or couplers of this invention based on the total weight of the dye concentrate and preferably 0.02% to about 5% on the same weight bases.

For the most part it has been found that the dyeing intensity on hair obtained with the present couplers when employed in an oxidation dye composition containing primary oxidation dye intermediates is related to the molar ratio of the primary oxidation dye intermediate to the coupler of this invention. It has been found that the molar ratio of primary intermediate to coupler that is useful for the purposes of this invention from 1:1 to 4:1. However, the greatest dyeing intensity is obtained where the molar ratio of primary intermediate to coupler is about 3:1 or 4:1.

It has also been found that there is a significant shift in shade as the ratio of primary intermediate to color coupler used in the hair dyeing procedure increases. This reflects the formation of the phenolic dye as well as the dye obtained from the reaction of the m-diamine coupler of this invention with the primary intermediate during the dyeing operation.

These features are generally, reflected in Tables I to III below. These tables record the Hunter values measured on hair samples dyed with oxidation dye compositions containing a primary oxidation dye intermediate (p-aminophenol also identified as PAP) and various couplers incorporated by the present invention and in which the molar ratios of PAP and the couplers of this invention are varied. The L value is a measure of the intensity of the color. The smaller the L value the greater the intensity of the color of the dyeing. The "a" and "b" Hunter values are a measure of the shade of the color of the dyed hair. An increase in the "a" value indicates an increase in the redness of the dyeing. A decrease in the "a" value would indicate an increase in the greenness of the dyeing. Correspondingly an increase in the "b" Hunter value signals an increase in the yellowness of the dyeing while a decrease in the "b" value would show an increase in the blueness of the dyeing.

The values for Ar given in each of the tables identify the aryl group that is contained in the coupler of this invention employed in the particular testing that is summarized in the respective studies. The complete formula for the coupler is arrived at by substituting the Ar values given in these tables in formula (I) above. The symbol [1] refers to the absolute concentration of the coupler.

TABLE I

Effect of dyeout intensity of primary intermediate to coupler ratio in reaction of p-aminophenol (PAP) with 1 (Ar = 3-amino-6-methyl phenyl) on gray hair. [1] = 0.25%

| Relative Moles | | Hunter Values | | |
|---|---|---|---|---|
| PAP | 1 | L | a | b |
| 1 | 1 | 32.2 | 2.3 | 7.3 |
| 2 | 1 | 30.8 | 2.6 | 8.0 |
| 3 | 1 | 28.5 | 3.0 | 8.4 |

TABLE II

Effect on dyeout shade of primary intermediate to coupler ratio in reaction of p-aminophenol with 1 (Ar = 3-amino-6-methyl-phenyl) on gray hair. [1] = 1.00%

| Relative Moles | | Hunter Values | | |
|---|---|---|---|---|
| PAP | 1 | L | a | b |
| 2 | 1 | 24.0 | 6.0 | 7.4 |
| 3 | 1 | 20.2 | 6.1 | 7.1 |

TABLE III

Effect on dyeout shade of primary intermediate to coupler ratio in reaction of p-aminophenol with 1 (Ar = 1-naphthyl) on bleached hair. [1] = 1.00%

| Relative Moles | | Hunter Values | | |
|---|---|---|---|---|
| PAP | 1 | L | a | b |
| 2 | 1 | 17.6 | 11.1 | 5.2 |
| 3 | 1 | 21.6 | 11.1 | 7.6 |
| 4 | 1 | 20.7 | 10.4 | 7.5 |

The observations with respect to the variation of the intensity of the dyeout and the molar ratio of primary intermediate to coupler of the present invention is explainable by the fact that several color coupling reactions take place. This will also explain why the colors obtained are drab and, therefore, natural in appearance. Assuming that the primary intermediate is p-phenylenediamine (PPD), and Ar=phenyl the reaction may be represented by the following equations:

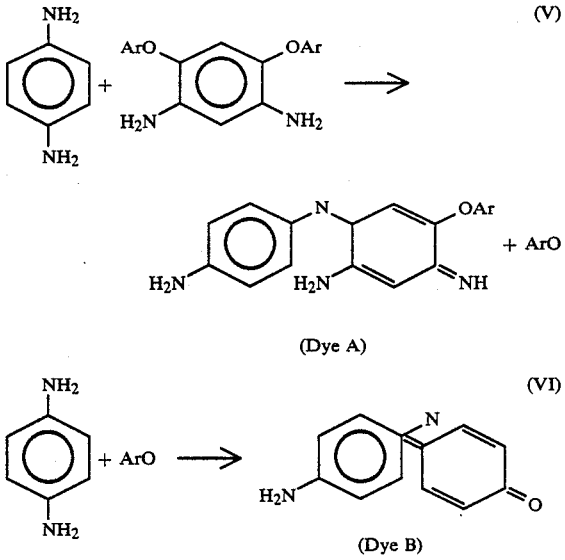

At higher ratios of primary intermediate a still further reaction takes place which are illustrated by the following equations:

$$\text{PPD} + \text{Dye A} \rightarrow \text{Dye C} + {}^{-}\text{OAr} \quad \text{(VII)}$$

$$\text{PPD} + {}^{-}\text{OAr} \rightarrow \text{Dye B} \quad \text{(VIII)}$$

It is by virture of the additional color coupling reactions that take place with the increase in molar ratios of primary intermediate to the coupler of this invention that the increase in intensity of dyeings are generally obtained and the more drab colors are formed in the hair.

The couplers of the present invention may be used in conjunction with any of the primary intermediates well known to those skilled in the hair dye art. There will generally also constitute part of the dye concentrate that is intended to be mixed with aqueous hydrogen peroxide before being applied to the hair. By way of illustrating primary intermediates that may be applied along with the coupling agents of the present invention may be made of p-phenylenediamine, p-aminophenol, N,N,bis(hydroxyethyl)-p-phenylenediamine, p-toluenediamine, p-aminodiphenylamine, 2,6-dimethy-p-phenylenediamine, 2,5-diaminopyridine, 2-chloro-p-phenylenediamine, 2-methoxy-p-phenylenediamine, 4,4'-diaminodiphenylamine.

Each of the aforesaid primary intermediates may be used alone or in combination with other primary intermediates. The term primary intermediate component is used herein to refer to a single or combination of primary intermediates.

The quantity of primary intermediate component that will be contained in the hair dye concentrate that will contain the couplers of the present invention may vary somewhat. Generally it will constitute from about 0.01% to about 10% by weight based on the total weight of the dye concentrate and preferably from about 0.02% to about 5% on the same weight bases.

The dye concentrate containing the coupler or couplers of this invention will also contain a cosmetic vehicle or carrier. This will ordinarily be a liquid vehicle in which the major component will be water. In addition the vehicle may also contain other adjuvants commonly contained in oxidation hair dye concentrates. These include such things as solvents, solubilizing agents, alkalizing agents, surfactants, stabilizing agents, chelating agents, other dyes e.g. direct dyes, perfumes, conditioning agents, etc.

In employing a dye concentrate including the coupler or couplers of this invention the dye concentrate will be mixed with aqueous hydrogen peroxide in the ratio of from about 0.25 parts to about 5 parts of concentrate per part of aqueous hydrogen peroxide. The concentration of hydrogen peroxide in said aqueous hydrogen peroxide will be in the range of from 1% to about 12% by wt. This mixture is applied to the hair and then shampooed in. The peroxide-dye concentrate mixture is allowed to remain on the hair for about 5 to about 60 minutes and the hair is then rinsed with water.

The following examples are given to further illustrate this invention. It is to be understood, however, that the invention is not limited thereto. In the equations given in each example the product of each stage is used as the starting material for the succeeding stage.

EXAMPLE 1

Preparation of 4,6-diphenoxy-1,3-benzenediamine dihydrochloride

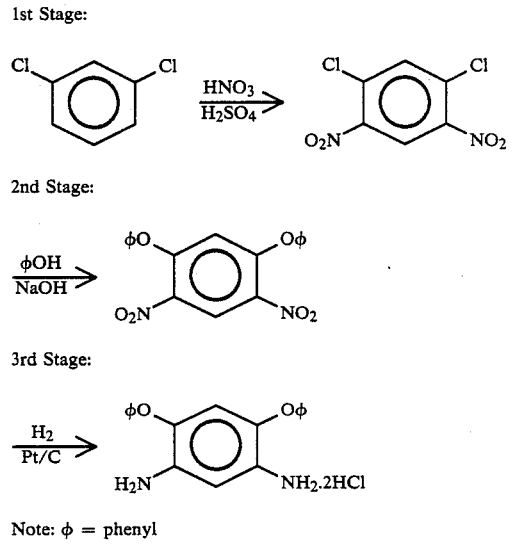

Note: ϕ = phenyl

1st stage: Synthesis of 2,4-dinitrol-1,5-dichlorobenzene:

To a mixture of 150 ml fuming $HNO_3$ (d=1.48) and 150 ml conc. $H_2SO_4$ cooled to 10°-15° C. was added 100 ml (128.8 g) (0.88 moles) m-dichlorobenzene over one (1) hr. The temperature was maintained at 10°-15° C. by external cooling throughout the addition. The temperature was then allowed to equilibrate to room temperature before externally heating. The mixture was then heated to 80° C. and the reaction monitored by TLC (hexanes). TLC shows reaction complete within 2 hrs. The mixture was cooled to 10° C., and the yellow product collected on a filter and washed with 100 ml water. The product was then washed free of residual acid by stirring in 1 L water @ 70°-80° C. for 2 hrs. Yield of 2,4-dinitro-1,5-dichlorobenzene after drying was 232.3 g (98%). m.p. 98°-100°.

2nd Stage: Synthesis of 4,6-diphenoxy-1,3-dinitrobenzene.

Under argon, add 24.4 (0.25 moles) of phenol and 250 ml toluene to a solution of 9.6 g (0.24 moles) NaOH in 25 ml water with stirring. Azeotrope off water; cool to ambient temperature. Add 23.7 g (0.10 moles) 1,5-dichloro-2,4-dinitrobenzene, then reflux for 2 hours. TLC (silica support, toluene eluent) shows only one spot. Vacuum filter, then cool to −5° C. Filter pale yellow crystals and dry in vacuo. at 50° C. Yield is 18.5 g (53%).

3rd Stage: Synthesis of 4,6-diphenoxy-1,3-benezenediamine dihychochloride.

Suspend 2 g ($5.7\times10^{-3}$ moles) of 4,6-diphenoxy-1,3-dinitrobenzene in 75 ml abs. ethanol; then add 5% Pt/C catalyst. Heat to 50° C. on Parr hydrogenator; then reduce. Filter into 400 ml HCl-saturated ethyl acetate, then remove solvent under vacuum. Yield is 2.05 g (90%) of tan powder.

EXAMPLE 2

Preparation of
4,6-bis(3-aminophenoxy)-1,3-benezenediamine
tetrahydrochloride

1st Stage:

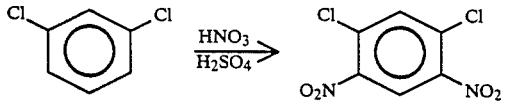

2nd Stage:

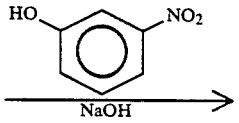

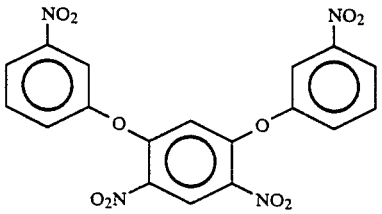

3rd Stage:

-continued

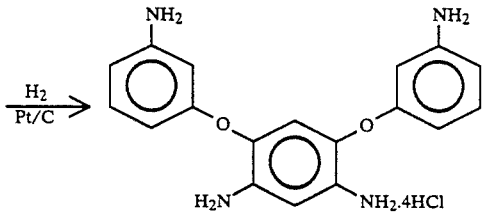

1st stage: Synthesis of 2,4-dinitro-1,5-dichlorobenzene as described in Example 1 above.

2nd stage: Synthesis of 4,6-bis(3-nitrophenoxy)-1,3-dinitrobenzene.

Under argon, add 34.7 g (0.25 moles) 3-nitrophenol and 250 ml toluene to a solution of 9.6 g (0.24 moles) NaOH in 25 ml water with stirring. Azeotrope off water and cool to ambient temperature. Add 23.7 g (0.1 moles) 2,4-dinitro-1,5-dichlorobenzene and reflux until TLC (silica support; toluene eluent) shows only one spot Vacuum filter and cool to −5° C. Filter crystals and dry in vacuo at 50° C.

3rd Stage: Synthesis of 4,6-bis(3-aminophenoxy)-1,3-benezendiamine tetrahydrochloride.

Suspend 2 g ($4.5\times10^{-3}$ moles) of 4,6-bis(3-nitrophenoxy)-1,3-dinitrobenezene in 75 ml absolute ethanol; then add 5% Pt/C. Heat to 50° C. on Parr hydrogenator, then reduce. Filter into 400 ml HCl-saturated ethyl acetate, then remove solvent under vacuum. Yield is 2.10 g (100%) of tan crystals.

EXAMPLE 3

Preparation of
4,6-bis(1-naphthyloxy)-1,3-benezenediamine
dihydrochloride

1st Stage:

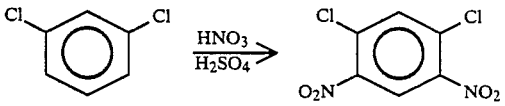

2nd Stage:

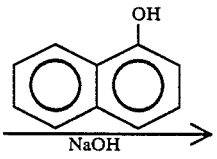

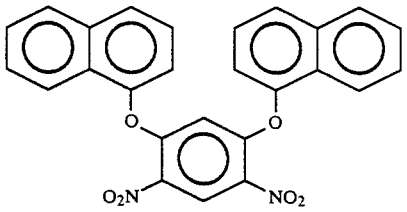

3rd Stage:

-continued

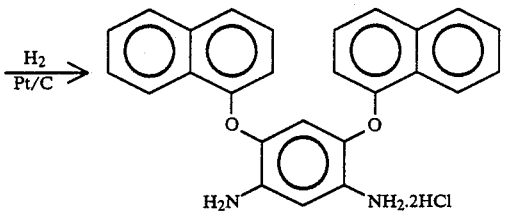

1st stage: Synthesis of 2,4-dinitro-1,5-dichlorobenzene as described above in Example 1.

2nd stage: Synthesis of 4,6-bis (1-naphthyloxy)-1,3-dinitrobenezene.

Under argon, add 36 g (0.25 moles) 1-naphthol and 250 ml toluene to a solution of 9.6 g (0.24 moles) NaOH in 25 ml water with stirring. Azeotrope off water and cool to ambient room temperature. Add 23.7 g (0.1 moles) 2,4-dinitro-1,5-dichlorobenezene and reflux until TLC (silca support; toluene eluent) shows only one spot. Vacuum filter and cool to −5° C. Filter crystals and dry in vacuo at 50° C.

3rd stage: Synthesis of 4,6-bis(1-naphthyloxy)-1,3-benezenediamine dihydrochloride Suspend 2 g ($4.4\times10^{-3}$ moles) 4,6-bis(1-naphthyloxy)-1,3-dinitrobenzene in 75 ml abs. ethanol, then add 5% Pt/C. Heat to 50° C. on Parr hydrogenator, then reduce. Filter into 400 ml HCl-saturated ethyl acetate, then remove solvent under vacuum. Yield is 2.05 g (100%) of tan crystals.

EXAMPLE 4

Preparation of 4,6-bis(2,6-dimethylphenoxy)benzenediamine dihydrochloride

1st Stage:

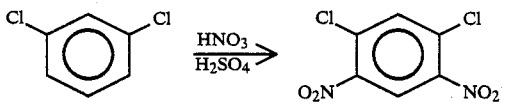

2nd Stage:

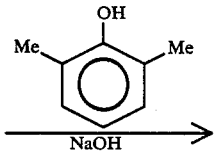

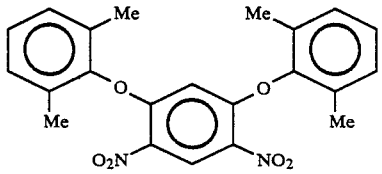

3rd Stage:

-continued

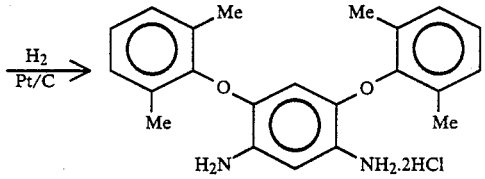

1st Stage: Synthesis of 2,4-dinitro-1,5-dichlorobenzene as described above in Example 1.

2nd Stage: Synthesis of 4,6-bis (2,6-dimethylphenoxy)-1,3-dinitrobenezene.

Under argon, add 30.5 g (0.25 moles) 2,6-dimethylphenol and 250 ml toluene to a solution of 9.6 g (0.24 moles) NaOH in 25 ml water. Azeotrope off water and cool to ambient temperature. Add 23.7 g (0.10 moles) of 2,4-dinitro-1,5-dichlobenzene and reflux until TLC (silica support; toluene eluent) shows only one spot. Vacuum filter and cool to −5° C. Filter crystals and dry in vacuo at 50° C.

3rd stage: Synthesis of 4,6-bis(2,6-dimethylphenoxy)-1,3-benzenediamine dihydrochloride.

Suspend 2 g ($4.9\times10^{-3}$ moles) 4,6-bis(2,6-dimethylphenoxy)-1,3-dinitrobenezene in 75 ml abs. ethanol, then add 5% Pt/C. Heat to 50° C. on Parr hydrogenator, then reduce. Filter into 400 ml HCL-saturated ethyl acetate, then remove solvent under vacuum. Yield is 2 g (97%) of tan solid.

EXAMPLE 5

Preparation of 4,6-bis(2,4-dimethylphenoxy)-1,3-benezenediamine dihydrochloride 1st Stage:

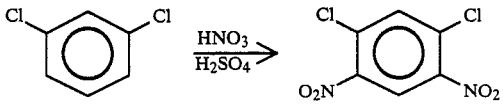

2nd Stage:

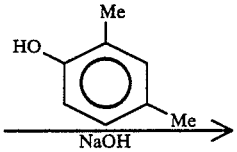

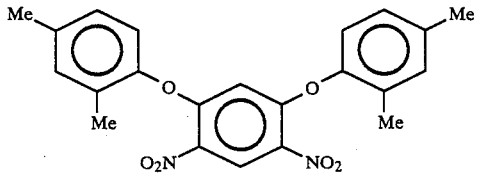

3rd Stage:

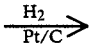

-continued

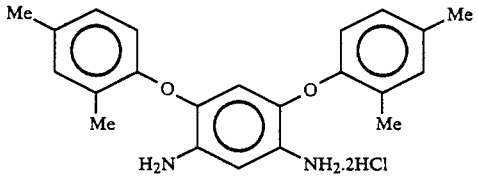

1st stage: Synthesis of 2,4-dinitrol-1,5-dichlorobenzene as described above in Example 1.

2nd stage: Synthesis of 4,6-bis(2,4-dimethylphenoxy)-1,3-dinitrobenzene.

Under Argon, add 30.5 g (0.25 moles) 2,4-dimethylphenol and 250 ml of toluene to a solution of 9.6 g (0.24) moles NaOH in 25 ml water. Azeotrope off water and cool to ambient temperature. Add 23.7 g (0.10 moles) 2nd stage:2,4-dinitro-1,5-dichlorobenzene and reflux until TLC (silica support; toluene eluent) shows only one spot. Vacuum filter and cool to −5° C. Filter crystals and dry in vacuo at 50° C.

3rd stage: Synthesis of 4,6-bis (2,4-dimethylphenoxy)-1,3-benezenediamine dihydrochloride.

Suspend 2 g ($4.9\times10^{-3}$ moles) 4,6-bis (2,4-dimethylphenoxy)-1,3-dinitrobenezene in 75 ml abs. ethanol, then add 5% Pt/C. Heat to 50° C. on Parr hydrogenator, then reduce. Filter into 400 ml HCl-saturated ethyl acetate, then remove solvent under vacuum. Yield is 2 g (97%) of tan solid.

EXAMPLE 6

Preparation of 4,6-bis (2-methylphenoxy)-1,3-benezenediamine dihydrochloride 1st Stage:

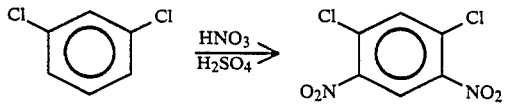

2nd Stage:

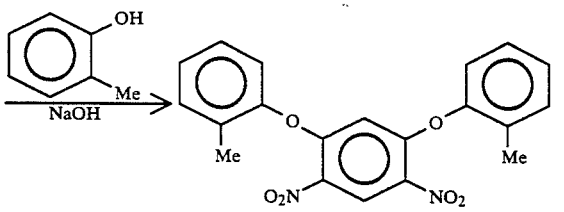

3rd Stage:

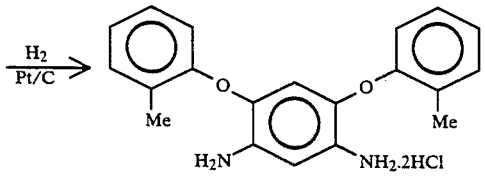

1st stage: Synthesis of 2,4-dinitrol-1,5-dichlorobenzene as described above in Example 1.

2nd stage: Synthesis of 4,6-bis (2-methylphenoxy)-1,3-dinitrobenzene.

Under argon, add 27 g (0.25 moles) o-cresol and 250 ml toluene to a solution of 9.6 g (0.24 moles) NaOH in 25 ml water with stirring. Azeotrope off water; cool to ambient temperature. Add 23.7 g (0.10 moles) 2,4-dinitro-1,5-dichlorobenzene and reflux until TLC (silica support; toluene eluent) shows only one spot. Vacuum filter and cool to −5° C. Filter crystals and dry in vacuo at 50%$^{C}$.

3rd stage: Synthesis of 4,6-bis(2-methylphenoxy)-1,3-benezenediamine dihydrochloride Suspend 2 g ($5.3\times10^{-3}$ moles) 4,6-bis(2-methylphenoxy)1,3-dinitrobenzene in 75 ml abs. ethanol, then add 5% Pt/C. Heat to 50° C. on Parr hydrogenator, then reduce. Filter into 400 ml HCl-saturated ethyl acetate, then remove solvent under vacuum. Yield is 2.05 g (99%) of tan powder.

EXAMPLE 7

Preparation of 4,6-bis(2-methyl-5-aminophenoxy)-1,3-benezenediamine tetrahydrochloride 1st Stage:

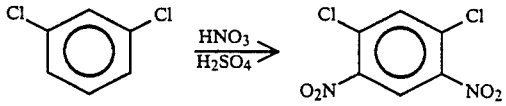

2nd Stage:

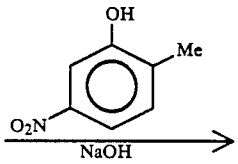

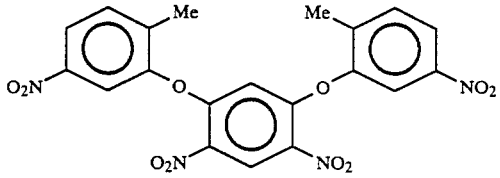

3rd Stage:

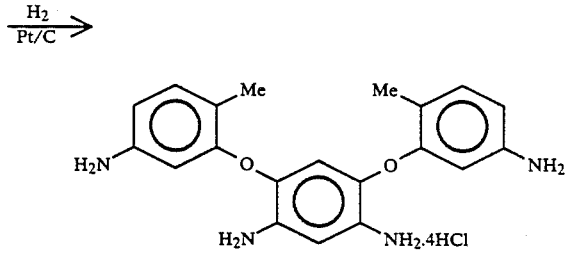

1st stage: Synthesis of 2,4-dinitro-1,5-dichlorobenzene as described above in Example 1.

2nd stage: Synthesis of 4,6-bis(2-methyl-5-nitrophenoxy)-1,3-dinitrobenzene

Under argon 8.0 g (0.052 moles) 5-nitro-o-cresol was reacted with 2.0 g (0.05 moles) NaOH in 100 ml toluene and the water Azeotroped off. Cool to ambient temperature, then add 4.74 g (0.02 moles) 1,5-dicholoro-2,4-dinitrobenzene. Add 25 ml DMSO (distilled over sodium). TLC shows reaction complete within 4 hours. The mixture was stirred into 500 ml ice and 25 ml ethanol was used to wash the solution from the reaction flask into the ice/water. Filter and dry in vacuo at 50° C.

3rd stage: Synthesis of 4,6-bis(2-methyl-5-aminophenoxy)-1,3-benzenediamine tetrahydrochloride.

Suspend 2 g ($4.3\times10^{-3}$ moles) 4,6-bis(2-methyl-5-nitrophenoxy)-1,3-dinitrobenzene in 25 ml ethyl acetate, then add 5% Pt/C. Heat to 50° C. on Parr hydrogenator, then reduce. Hot filter under argon, then cool to ambient temperature. Add 1.43 ml conc. HCl with stirring, then azeotrope off water under vacuum. Filter, wash with ethyl acetate, and dry in vacuo at 20° C. Yield is 1.56 g (73%).

The following dyeing examples are given in Table IV. The dyeing solution consisted of 1% by weight of the m-diamine coupler in 35% aqueous ethanol. The designated primary intermediates PPD, PAP, BHE are employed in the concentrations of 2,3, or 4 equivalents as indicated in the following Table. 3% $H_2O_2$ is used as the oxidant. Swatches of grey and bleached hair were dyed with these compositions. The dyeing procedure used involved soaking the hair swatch in twice its weight of a mixture if equal parts of a 6% $H_2O_2$ solution and the appropriate dye mixture for a period of 30 minutes. After this time, the swatch was rinsed and then shampooed and dried. Hunter Tristimulus readings were then taken on the hair swatch or its color was evaluated visually. The following abbreviations have the meanings indicated:

PPD=p-phenylenediamine

PAP=p-aminophenol

BHE=N,N,bis-(beta-hydroxyethyl)-p-phenylenediamine

The color of the hair dyeings obtained with the respective compositions are set out in the Table under the heading "Shade Produced".

TABLE IV

| Ex. No. | $R_1$ | $R_2$ | Primary Intermed./ # Equivalents | Shade Produced Grey | Bleached |
|---|---|---|---|---|---|
| 8. | 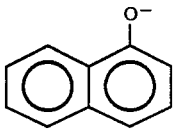 | 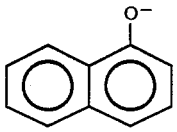 | PPD/2 equiv. | med. warm brown | dk. warm brown |
| | | | PAP/2 equiv. | med. orange | med. red orange |
| | | | BHE/2 equiv. | med. drab orange | dk. drab blue |
| | | | PPD/3 equiv. | med. warm brown | dk. warm brown |
| | | | PAP/3 equiv. | lt. orange | lt. red orange |
| | | | BHE/3 equiv. | med. drab blue | dk. blue black |
| | | | PPD/4 equiv. | dk. brown | black |
| | | | PAP/4 equiv. | lt. orange brown | med. orange |
| | | | BHE/4 equiv. | med. olive green | dk. green |
| 9. | 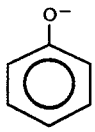 | 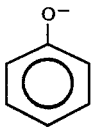 | PPD/2 equiv. | dk. brown | black |
| | | | PAP/2 equiv. | med. golden brown | med. golden yellow |
| | | | BHE/2 equiv. | med. drab blue | dk. blue |
| 10. | 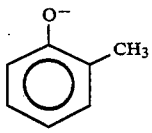 | 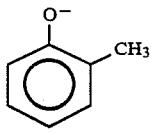 | PPD/2 equiv. | dk. charcoal grey | dk. violet grey |
| | | | PAP/2 equiv. | lt. brown | med. golden brown |
| | | | BHE/2 equiv. | lt. blue | med. drab blue |
| 11. | 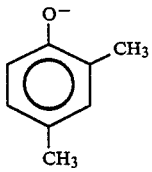 | 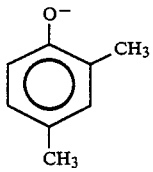 | PPD/2 equiv. | dk. brown | drab black |
| | | | PAP/2 equiv. | lt. brown | dk. golden yellow |
| | | | BHE/2 equiv. | med. drab green | dk. green |
| | | | PPD/2 equiv. | drab dk. brown | dk. brown |
| | | | PAP/2 equiv. | dk. golden brown | lt. reddish brown |
| | | | BHE/2 equiv. | med. grey blue | icy blue |
| 12. | 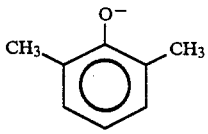 | 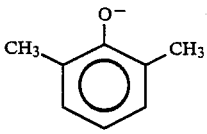 | PPD/3 equiv. | black | black |
| | | | PAP/3 equiv. | med. yellow orange | med. reddish brown |
| | | | BHE/3 equiv. | med. grey blue | dk. blue green |
| | | | PPD/4 equiv. | charcoal grey | black |
| | | | PAP/4 equiv. | med. orange brown | med. reddish brown |
| | | | BHE/4 equiv. | med. grey blue | dk. blue green |
| | | | PPD/2 equiv. | violet black | black |
| | | | PAP/2 equiv. | lt. orange brown | med. orange |
| | | | BHE/2 equiv. | dk. blue | dk. blue |
| 13. | 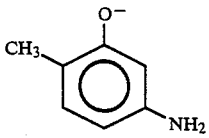 | 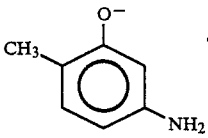 | PPD/3 equiv. | drab black | black |
| | | | PAP/3 equiv. | dk. orange | med. orange |
| | | | BHE/3 equiv. | dk. blue | blue black |

What is claimed is:

1. A compound of the formula:

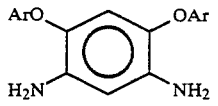

wherein the Ar's are the same or different and are substituted or unsubstituted aryl radicals, selected from the group consisting of phenyl groups substituted with one or more of dialkyl, amino, alkoxy, hydroxyalkoxy, halo, and hydroxy groups and substituted or unsubstituted naphthyl groups wherein the substituents on the naphthyl group are one or more groups selected from the group consisting of $C_{1-5}$ alkoxy groups, $C_{1-5}$ hydroxy alkyl groups containing 1 to 5 amino, halo, or hydroxy groups, and mixtures thereof.

2. A compound according to claim 1 wherein the numbers of carbon atoms in the ring structure of said monocyclic or bicyclic aryl radicals are in the range of from about 6 to about 10 carbon atoms.

3. A composition according to claim 1 wherein Ar is naphthyl.

4. A composition according to claim 1 wherein Ar is 2,6-dimethylphenyl.

5. A composition according to claim 1 wherein Ar is 3-aminophenyl.

6. A composition according to claim 1 wherein Ar is 3-amino-6-methylphenyl.

7. A composition according to claim 1 wherein Ar is 3-hydroxyphenyl.

8. A composition according to claim 1 wherein Ar is 2-methyl-3-hydroxyphenyl.

9. An oxidation hair dye concentrate containing at least one oxidation dye primary intermediate and as a color coupler component one or more of the compounds defined in claims 1, 2, 3, 4, 5, 6, 7 or 8 above.

10. An oxidation hair dye concentrate containing at least one oxidation dye primary intermediate and as a color coupler component one or more compounds defined in claims 1, 2, 3, 4, 5, 6, 7 or 8 wherein the color coupler component is present in said oxidation dye concentrate in the range of from about 0.01% to about 10% by weight of said color coupler component based on the total weight of said hair dye concentrate.

11. An oxidation hair dye concentrate containing at least one oxidation dye primary intermediate and as a color coupler component one or more of the compounds defined in claims 1, 2, 3, 4, 5, 6, 7 or 8 wherein the molar ratio of said primary intermediate to said color coupler component contained in said concentrate is in the range of from about 1:1 to about 4:1.

12. An oxidation hair dye concentrate containing at least one oxidation dye primary intermediate and as a color coupler component and one or more of the compounds defined in claims 1, 2, 3, 4, 5, 6, 7 or 8 wherein the molar ratio of said primary intermediate to said color coupler component in said concentrate is in the range of from about 3:1 to about 4:1.

13. A process for dyeing hair which comprises applying to said hair oxidation hair dye composition containing at least one oxidation dye primary intermediate, an oxidizing agent and as a color coupler component one or more of the compounds defined in claims 1, 2, 3, 4, 5, 6, 7 or 8 said primary intermediate and said color coupler component being present in said composition at concentrations sufficient to effectively dye said hair.

14. The dye concentrate of claim 11 wherein the primary intermediate is selected from the group consisting of: p-phenylene diamine, p-aminophenol, N,N-bis(-hydroxyethyl) p-phenylene-diamine, p-toluene diamine, p-aminodiphenyl amine, 2,6-dimethyl-p-phenylene diamine, 2,5-diaminopyridine, 2-chloro-p-phenylene diamine, 2-methoxy-p-phenylene diamine, 4,4'-diaminophenylamino or mixtures thereof.

15. The process of claim 13 wherein the primary intermediate is selected from the group consisting of: p-phenylene diamine, p-aminophenol, N,N-bis(hydroxyethyl) p-phenylene diamine, p-toluene diamine, p-aminodiphenyl amine, 2,6-dimethyl-p-phenylene-diamine, 2,5-diaminopyridine, 2-chloro-p-phenyl diamine, 2-methoxy-p-phenylene diamine, 4,4'-diaminophenylamine or mixtures thereof.

* * * * *